United States Patent

Bier et al.

[11] Patent Number: 5,540,826
[45] Date of Patent: Jul. 30, 1996

[54] MULTI-CHANNEL SEPARATION DEVICE

[75] Inventors: Milan Bier; Terry D. Long; Rodolfo Marquez; Anthony R. Ford, all of Tucson, Ariz.

[73] Assignee: Protein Technologies, Inc., Tucson, Ariz.

[21] Appl. No.: 403,982

[22] Filed: Mar. 15, 1995

[51] Int. Cl.$^6$ ................................ B01D 61/42
[52] U.S. Cl. ................ 204/610; 204/616; 204/627; 204/644
[58] Field of Search ................ 204/301, 299 R

[56] References Cited

U.S. PATENT DOCUMENTS

| 4,204,929 | 5/1980 | Bier | 204/180 R |
|---|---|---|---|
| 4,362,612 | 12/1982 | Bier | 204/301 |
| 4,963,236 | 10/1990 | Rodkey et al. | 204/183.2 |
| 4,971,670 | 11/1990 | Faupel et al. | 204/182.8 |
| 5,087,338 | 2/1992 | Perry et al. | 204/182 B |
| 5,173,164 | 12/1992 | Egen et al. | 204/301 |
| 5,411,650 | 5/1995 | Frank | 204/182.4 |

*Primary Examiner*—Arun S. Phasge
*Attorney, Agent, or Firm*—Kenyon & Kenyon

[57] ABSTRACT

A multi-channel separation device is provided for use in separation technology, particularly in electrophoresis and in isoelectric focusing. The device includes two mating plates, at least one of which contains an array of at least three cavities arranged to define a serpentine fluid pathway through the cavities when the plates are mated. Each of the cavities includes fluid input and output ports to facilitate transfer of process fluid through the cavities. A septum is disposed between the plates for streamlining fluid flow between the input and output ports by restricting but not preventing free fluid flow between adjacent cavities. The device also includes anodic and cathodic compartments containing electrodes for establishing an electric field across the cavities.

34 Claims, 6 Drawing Sheets

MULTI-CHANNEL SEPARATION DEVICE

FIELD OF THE INVENTION

This invention relates to multi-compartment devices commonly utilized in separation technology and particularly in electrophoresis and in isoelectric focusing.

BACKGROUND OF THE INVENTION

There are many types of devices comprising two or more subcompartments that are separated from each other by septa like, for example, monofilament screens, membranes, gels, filters, and fritted discs. Generally, these devices are assembled from a plurality of essentially parallel frames or spacers, separated from each other by the septa. Some of these devices comprise a repetitive assembly of functional units requiring only two compartments, such as a repetitive assembly of input and output subcompartments in a filter press.

The invention is of particular relevance to electrophoretic devices where three or more subcompartments are aligned, and wherein transport of solutes potentially occurs across all the compartments. For instance, in U.S. Pat. No. 4,362,612 issued to Bier, the adjoining compartments are functionally designed to electrophoretically adjust to different pH values, thereby separating dissolved proteins according to their isoelectric points. Similar multiple subcompartments devices are described in U.S. Pat. No. 4,971,670 issued to Faupel et al., U.S. Pat. No. 5,173,164 issued to Egen et al., U.S. Pat. No. 4,963,236 issued to Rodkey et al., and U.S. Pat. No. 5,087,338 issued to Perry et al.

All of the above patents disclose devices comprising a series of parallel spacers that are separated from each other by septa, which results in an essentially parallel array of subcompartments. Apart from the cited patents, numerous other such devices have been disclosed in patents and other publications. In all such devices, electrodes are provided at the ends of the assembly of subcompartments for the application of an electrical field.

Each subcompartment of these devices usually includes an input port and an output port for circulation of process fluid. The septa have a primary function of streamlining the flow of liquid without unduly hindering the intercompartmental transport of solutes due to electrical or diffusional forces. The septa in these devices may also have other functions, depending on the intended use of the apparatus. In some instruments, like the above-identified Bier and Egen et al. devices, the septa are simply monofilament screens of fine porosity, and the relatively open nature of the septa are used to minimize interaction with the electric process. In the Faupel et al. device, on the other hand, the septa constitute buffered membranes of polyacrylamide gels impregnated on fiber-glass filters. The intended purpose of the buffered septa is to control the transport of proteins across the membranes, limiting this transport to only proteins of certain polarity. In yet other devices (Perry et al., for instance) membranes of controlled porosity are used to separate solutes according to particle size. In the present application, the generic term septum is utilized to describe all of the above possibilities, as these are all compatible with the invention at hand. In addition to such inter-compartment septa, most instruments require physical containment of electrolytes used around the electrodes, for which the term membrane will be used.

The production, assembly and use of such devices is complicated and made difficult by the multitude of component spacers and septa, all of which have to be assembled in a parallel sequence and sealed against fluid leaks.

SUMMARY OF THE INVENTION

The object of the present invention is to overcome this difficulty, and to provide a simpler design of devices incorporating three or more sequential subcompartments, separated from each other by septa. A device in accordance with the present invention is obtained by mating two planar surfaces, each surface provided with an array of adjacent cavities, and wherein the two surfaces are separated by the septum. Cavities on each of the surfaces are arranged to be out of sync with respect to cavities on the opposing surface, with the cavities being offset by a distance of roughly half a cavity width. In such a device, the sequential subcompartments formed by the cavities are no longer parallel to each other, but instead are arranged in a serpentine fashion, defining a hopscotched pathway moving to and fro across the septum. The multiple spacers and septa are accordingly reduced to as little as only the two mating surfaces and the septum, irrespective of the number of subcompartments. If an external electric field is applied, it will no longer be applied in a straight line from electrode to electrode, but will proceed essentially in a serpentine manner, winding across the septum to successive cavities in the two surfaces. Alternate designs accomplishing the same purpose are also disclosed herein.

While the design in accordance with the invention will result in lengthening the travel distance for migrating solutes, this is more than compensated by the simplicity of the design and use. For instance, this design makes it readily feasible to manufacture devices at sufficiently low cost to make them disposable. Disposable electrophoretic devices would greatly reduce the risk of product cross-contamination, simplify apparatus usage and contribute to the cleanliness and safety of overall operation.

In some applications, the septum is only a fluid flow streamliner, and has no other effect on the separation process. Thus, it may be possible to further simplify the device by eliminating the septum altogether. In such a case, the streamlining of the flow between successive subcompartments can be obtained by reducing the spacing between the mating surfaces of parts comprising the device, thus reducing the contact between successive sub-compartments to a narrow slit only. The resistance to fluid flow through a narrow slit is sufficient to essentially confine the flow through the wider cavities.

To apply such devices to electrophoresis and/or to isoelectric focusing, electrode compartments are included at both ends of the cavity array. It should be noted that the present design is applicable not only to electrophoresis, but also to other membrane devices where successive subcompartments may be desirable, such as, for example, in filters, electrodialyzers, and reverse osmosis devices.

BRIEF DESCRIPTION OF THE DRAWINGS

The foregoing and additional objects and advantages of the invention will become more apparent as the following detailed description is read in conjunction with the accompanying drawings wherein like reference characters denote like parts.

DETAILED DESCRIPTION

In conventional multi-compartment electrophoretic devices, the electric field is oriented in a perpendicular direction to a parallel array of septa by means of electrodes contained in anodic and cathodic compartments of the devices. In addition, the devices include subcompartments, each of which is provided with an inlet and an outlet port, and fluid flow is provided through each subcompartment by external pumping means. The flow can be in single pass or recycled by means of fluid recycling loops. Other components may be included in the external flow channels, such as heat exchangers, reservoirs extending the volume capacity of each recirculating loop, and sensors for pH, temperature, and/or UV absorption, etc.

Figure 1:
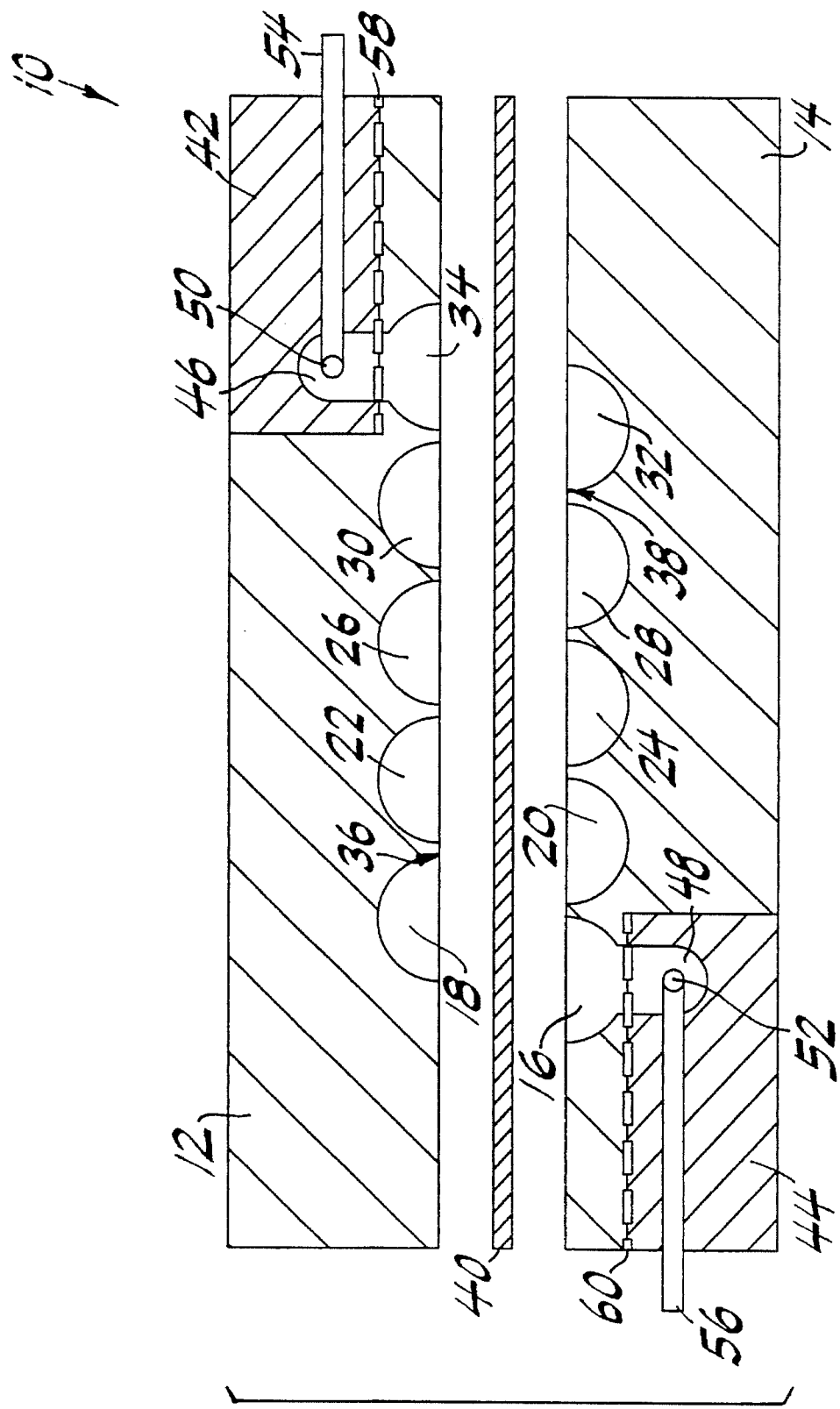
FIG. 1 is a schematic cross-section view of a device in accordance with one embodiment of the invention.

FIG. 1 illustrates a midline cross-section view of a multi-channel device 10 in accordance with one embodiment of the present invention. The device 10 includes two plate-shaped elements 12 and 14 that have mating planar surfaces. Each plate 12, 14 includes an array of roughly parallel cavities, which are labelled as 18, 22, 26, 30 and 34 on plate 12 and as 16, 20, 24, 28 and 32 on plate 14. While the cavities are shown to have a semicircular shape, the shape can be substantially varied as desired. It is important, however, that the distance separating adjacent cavities in each array, labelled 36 and 38, be significantly smaller than the width of each cavity. The cavity arrays of the two parts face each other, but are displaced with respect to each other, that is, each cavity on one plate is offset from a proximate cavity on the other plate, by a distance of about half a cavity width. A septum 40 is positioned between plates 12 and 14, separating the arrays of cavities.

In addition, block-shaped elements 42 and 44 are positioned in plates 12 and 14 to house electrolyte compartments 46 and 48, respectively. Electric current can be applied by means of electrodes 50 and 52, making contact with an external power supply (not shown) through connectors 54 and 56, respectively. The electrolyte compartments 46, 48 are separated from adjacent cavities 34, 16 by membranes 58 and 60, respectively. The membranes 58, 60 are permeable to current carrying ions, but impermeable to gross fluid flow.

In device 10, plates 12 and 14 are substantially identical. This, however, need not always be the case as it is equally feasible to place both electrode compartments on the same plate (either 12 or 14) by a suitable rearrangement of the cavities. Nor is there any limit to the number or dimensions of the cavities, which can be varied as required by the specific application of the device. There are preferably at least three cavities in the device since a device with two cavities may not achieve all of the advantages of the present invention.

Figure 2:
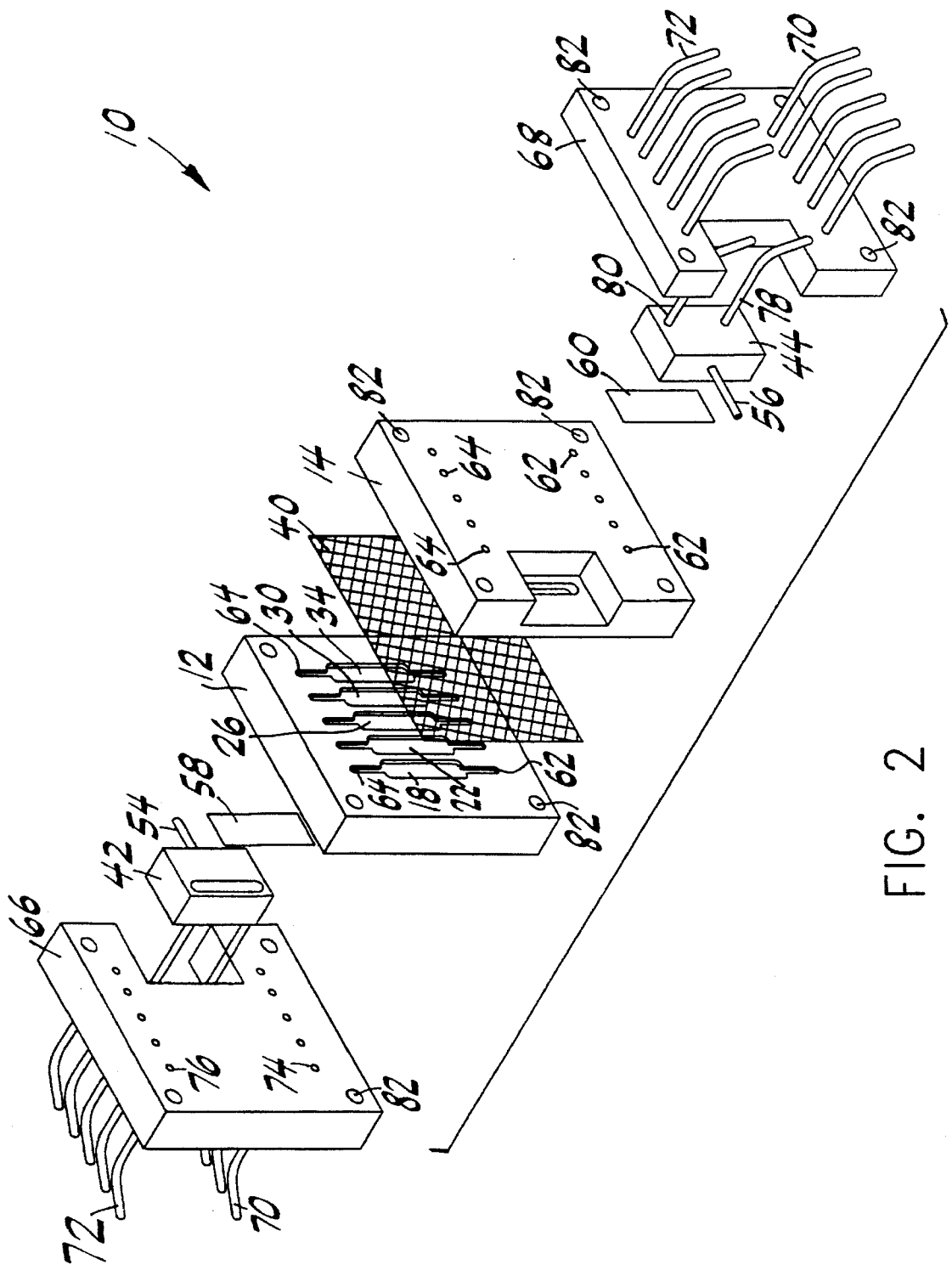
FIG. 2 is a schematic exploded view of the device shown in FIG. 1, illustrating further details of the invention.

FIG. 2 illustrates further details of the device shown in FIG. 1. Plates 12 and 14 are shown separated by septum 40. Each cavity 16–34 in plates 12 and 14 includes an essentially identical inlet port 62 and an essentially identical outlet port 64. The inlet and outlet ports are accessible by means of flexible tubing. Individual tubing can be attached to each inlet and outlet port, which however is a laborious task. Instead, FIG. 2 illustrates use of parts 66, 68 comprising "quick-connects" for multiple tubing. The parts 66, 68 include sets of inlet tubing 70 and outlet tubing 72, which lead to ports 74 and 76, respectively, which in turn are positioned to match corresponding inlet ports 62 and outlet ports 64, respectively, on the plates 12, 14.

Block-shaped elements 42, 44 are separated from the rest of the device by means of membranes 58, 60, respectively. Each electrolyte compartment 46, 48 also includes an inlet tubing connection 78 and an outlet tubing connection 80.

Repetitively placed holes 82 can be used for assembling the device by means of bolts (not shown). Obviously, there can be various other means of assembly, which means are not critical for the invention.

To assemble the device 10 of FIGS. 1 and 2, the two plates 12 and 14 are pressed together, sealing the septum 40. An electric field, when applied by means of the electrodes 50, 52, will not be oriented orthogonally to the septum 40 as in conventional multi-compartment cells such as described in the patents cited above, but will wind in a serpentine manner from cavity to cavity while taking the path of least resistance. Thus, the electric field will be approximately tangentially oriented relative to the septum 40 over most of its length. Any ionized material susceptible to electrophoretic transport will also migrate in a serpentine manner as long as its properties are compatible with its passage through the septum. If the process fluid is capable of generating a pH gradient, as in isoelectric focusing, the contents of each cavity will acquire a different pH. This can then be utilized for separation of proteins and other ampholytes, as is common in isoelectric focusing.

In the above design, the parts comprising the device may be machined from solid plastic such as plexiglass, molded out of a thermoplastic resin, or made by various other suitable manufacturing processes. The material should have chemical resistance to aqueous solutions, the electric field, and weak acids or bases. In addition, it is desirable to have optical clarity or at least some degree of transparency.

While the cavities in the plates 12, 14 need not have identical depths, they should preferably have matching widths and spacings. For instance, it may be preferable to have the cavities of one of the plates be deeper than in the other. In general, one may wish the depth of the cavity to be proportional to the width, with relatively minimal spacing in between the cavities, consonant with their manufacturing process.

Figure 3:
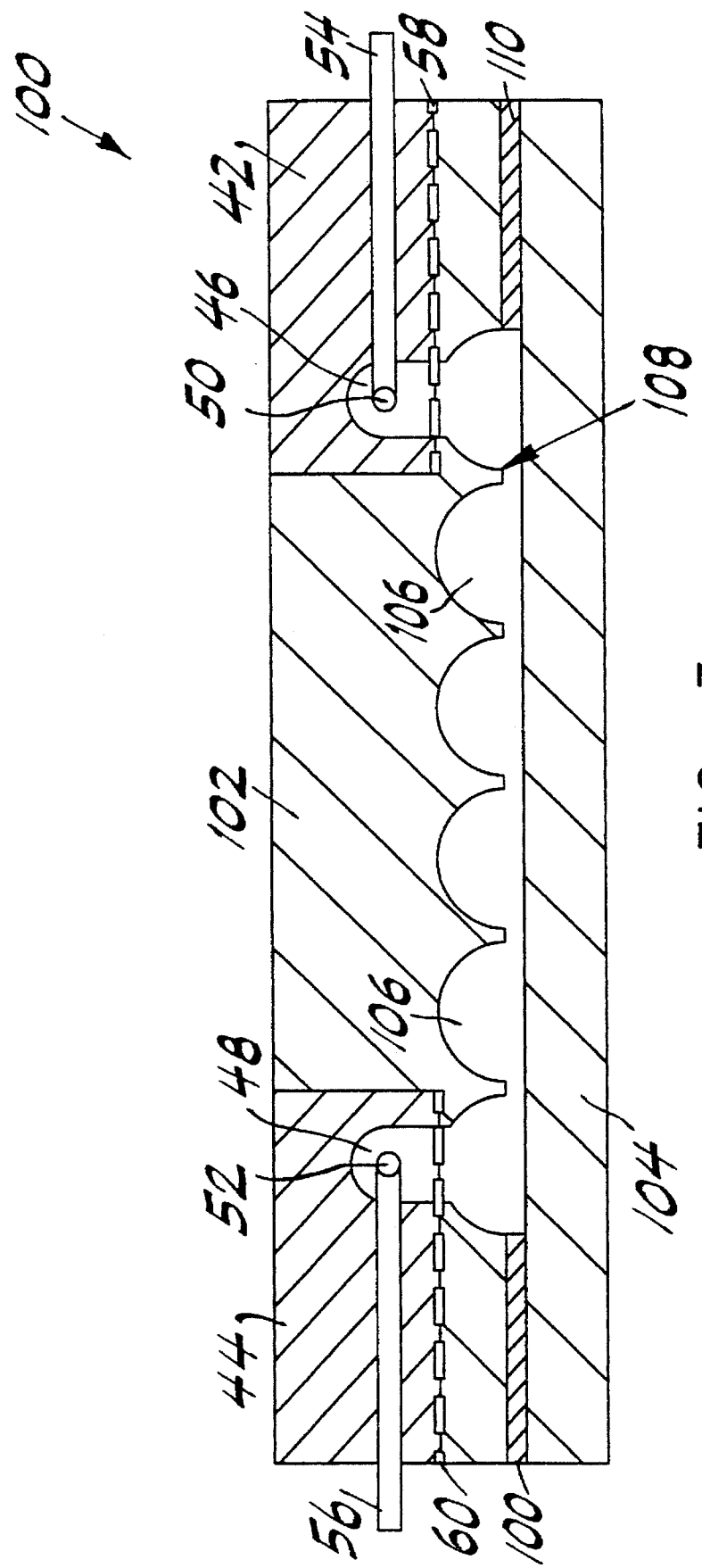
FIG. 3 is a schematic cross-section view of a device in accordance with another embodiment of the invention.

FIG. 3 illustrates a device 100 in accordance with a further embodiment of the invention. The device 100 includes plate-shaped elements 102 and 104, wherein all of the cavities of the device, all labelled as 106, are located in plate 102. The mating surface of plate 104 is flat. This configuration obviates the need for a septum between the two plates. The primary role of the septum is to streamline the flow of liquid, providing an increased resistance to flow of liquid from cavity to cavity. In the device 100 of FIG. 3, flow streamlining is achieved by reducing the transport area between adjacent cavities to only a narrow slit between the bridges 108 of the cavities 106 and the flat plate 104. This distance may be controlled, for instance, by means of a spacer 110, which seals the inter-plate space. Obviously, other design modifications can also achieve a serpentine fluid pathway through an arrangement of cavities.

Figure 4:
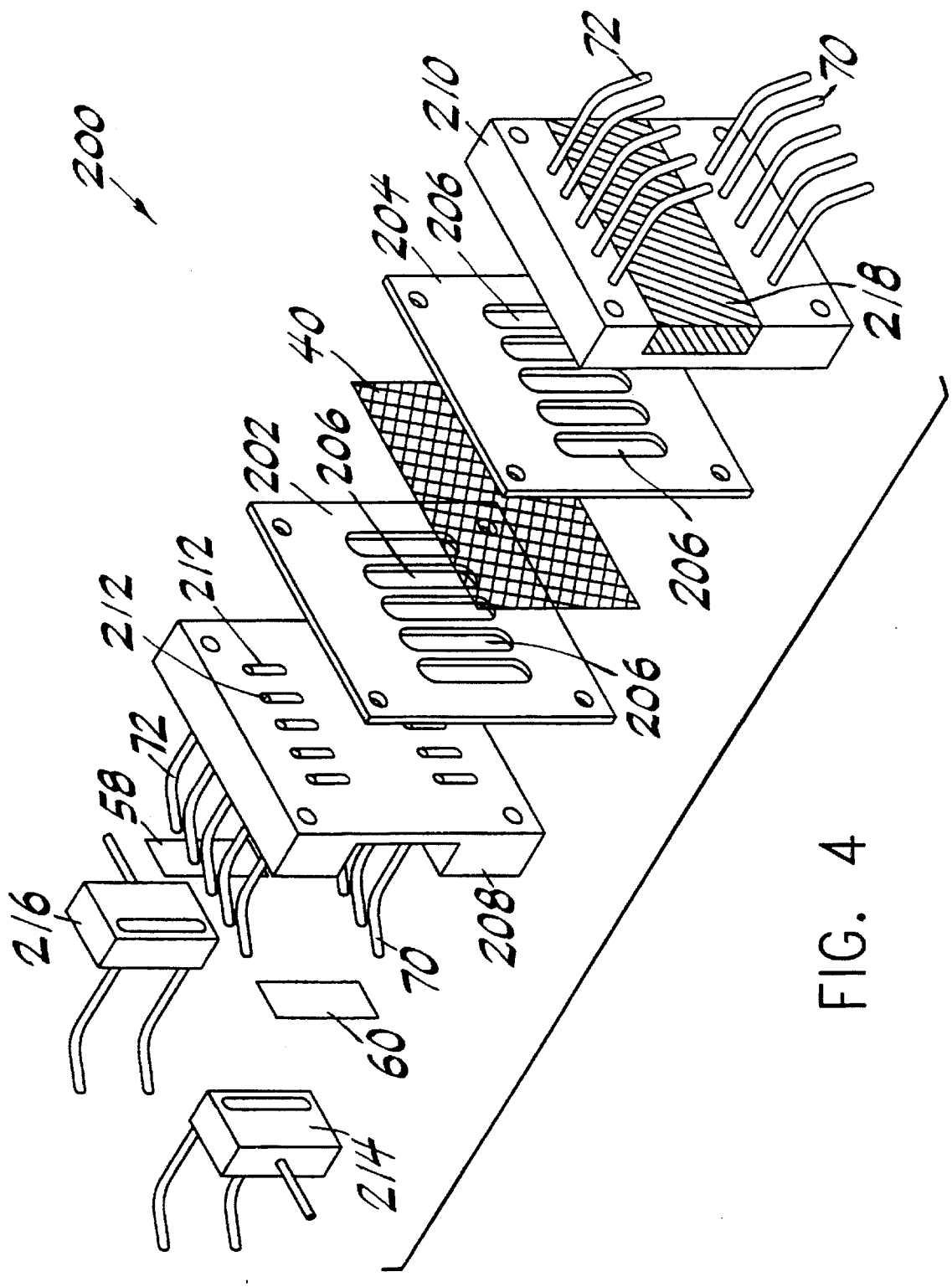
FIG. 4 ms a schematic exploded view of a device in accordance with yet another embodiment of the invention.

FIG. 4 illustrates a device 200 in accordance with a further embodiment of the invention also including a serpentine electric or fluid pathway. In this embodiment, the plates 12 and 14 of the FIG. 2 embodiment are replaced by element parts 202 and 204, each of which includes a plurality of throughholes 206 or cavities extending through the parts. This design provides a very simple assembly for the device, lending it suitable for use as a disposable item. The two parts 202, 204 could be made from an elastomer, which when pressed together would seal the screen and provide conduit to multi-channel quick-connects 208 and 210. The elastomer parts 202, 204 can be die-cut from elastomer sheeting or be injection molded from, for example, silicone rubber. The elastomer parts 202, 204 can be inserted between two end plates 208, 210 functioning as quick-connects and carrying attached tubing sets 70, 72. The end plates 208, 210 include appropriate channelling 212 to serve as fluid conduits between the throughholes 206 and the rest of the device.

This design also lends itself to easy cooling of process fluid in order to dissipate heat generated by electric current. Both electrode compartments 214, 216 can be mounted on one side of the device (part 208), leaving ample space for insertion of a cooling element 218 in the part 210. The cooling element 218 could be a metal plate cooled by a Peltier thermoelectric unit or by circulation of a refrigerant. Obviously, such a metal part could not come in direct contact with the process fluid, but could be located in a cut-out portion of part 210, which could act as an electrical insulator.

Figure 5:
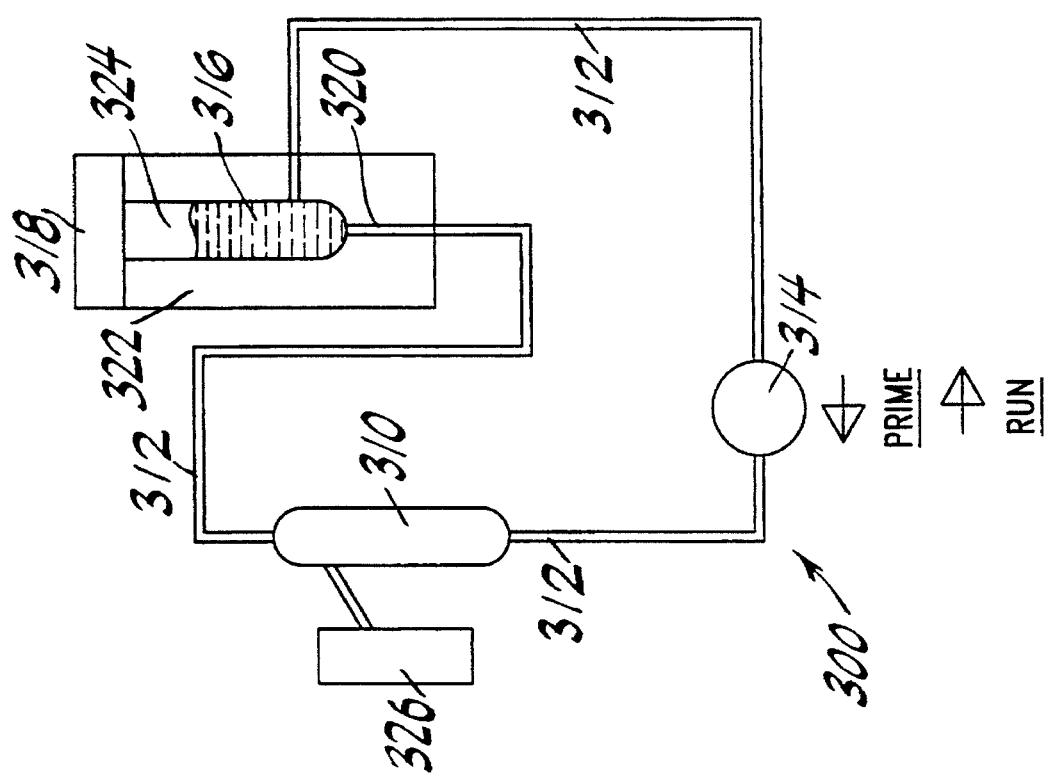
FIG. 5 is a schematic illustration of an apparatus for isoelectric focusing incorporating a multi-channel device of the present invention.

FIG. 5 illustrates an apparatus 300 used for isoelectric focusing including a multi-channel device 310 in accordance with the invention like, for example, the devices previously described. The multi-channel device 310 is connected by means of a tubing set 312 to a multi-channel pump 314 and a multiple pulse trap 316. An individual pulse trap, tubing loop and pump channel are assigned to each cavity and to the two electrode compartments in device 310. Optimally, each pulse-trap should have fluid capacity sufficient to prime the rest of the loop and the cavities in device 310. To prime the apparatus, all pulse-traps 316 are filled with process fluid and sealed by means of cover 318. Flow of fluid is started in the prime direction indicated at pump 314. The inlet to the loop is indicated at 320 and its return outlet to the pulse-trap is indicated at 322. Once fluid flow is established, the air evacuated from the recycling loops will form an air-pocket 324 at the top of each pulse-trap. At that time, the electric field can be applied from power supply 326 and the processing can be started. For isoelectric focusing, the process fluid should be capable of establishing or maintaining a pH gradient through appropriate buffering, as is well known in the art.

Alternatively, the septum in device 310 may contain a copolymerized pH gradient as taught by the Faupel et al. patent. Heat dissipation can be accomplished in various ways, either through direct cooling of the device 310 or through heat exchange with atmosphere or a cooling bath of tubing loops or the pulse-traps.

Figure 6:
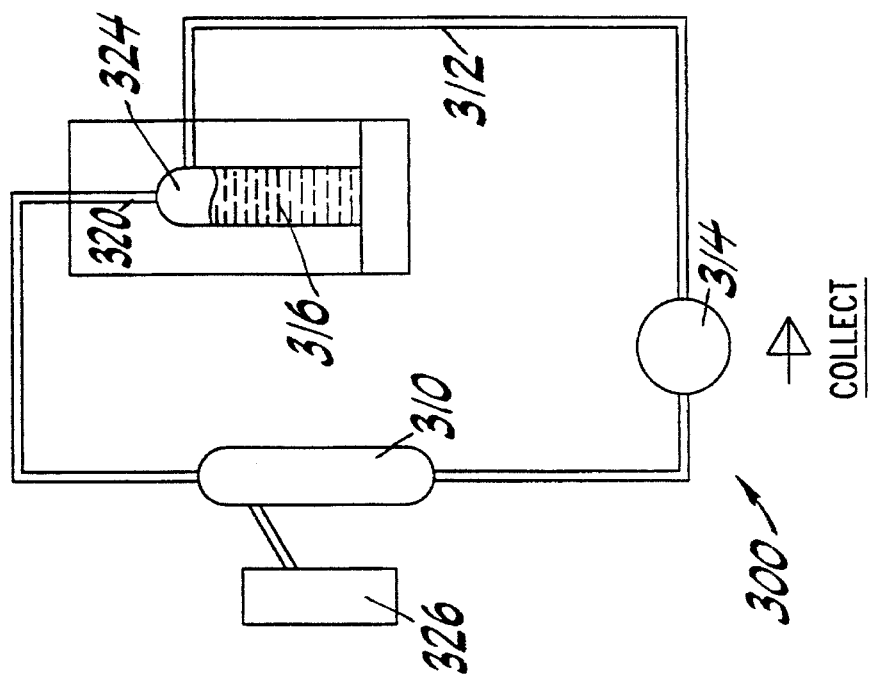
FIG. 6 is a schematic illustration of the FIG. 5 apparatus illustrating the operation of collecting separated fractions.

An important step in operation of the apparatus 300 is the collection of separated fractions. This should be carried out as smoothly as possible without interruption of fluid flow and major change in fluid pressures. As an essential step in the inventive process, part 316 is simply turned upside down, without interruption of fluid flow or, preferably, without interruption in electric power as shown in FIG. 6. This rotation reverses the priming process, replacing process fluid contents of each recycling loop with the air from the air-pockets 324, which now face the loop inlets 320. Such collection minimizes remixing of separated fractions contained in each recycling loops.

Figure 7:
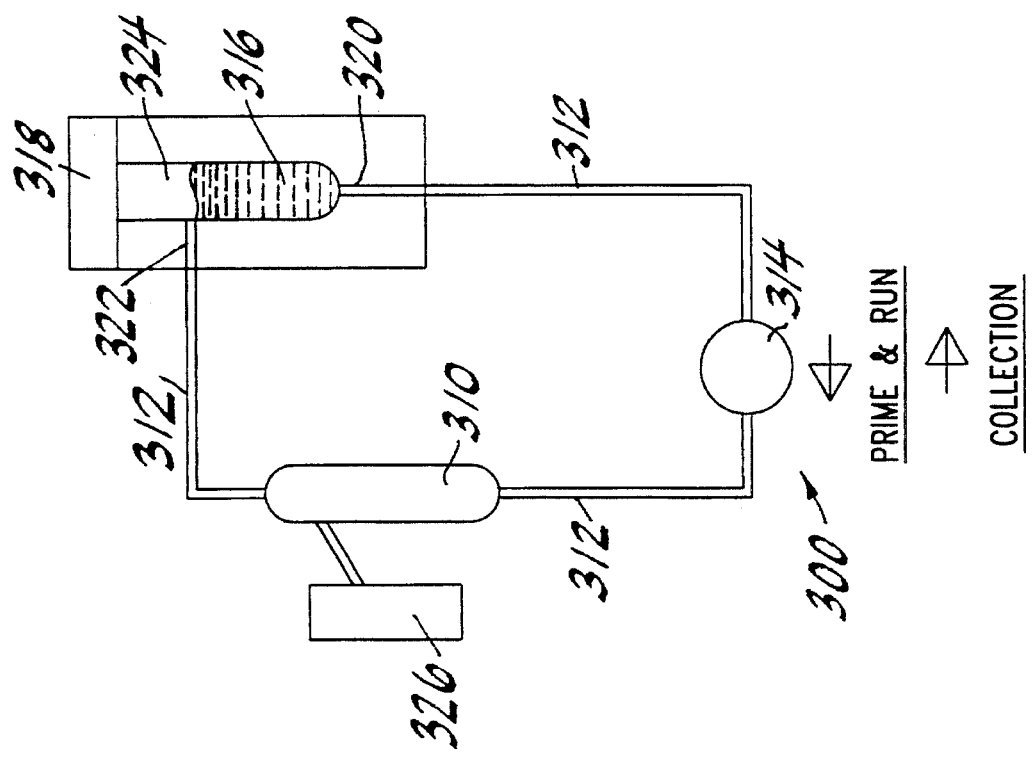
FIG. 7 is a schematic illustration of an apparatus for isoelectric focusing illustrating an alternate method of collection of fractions.

As an alternative, as shown in FIG. 7, collection of all fractions into the part 316 can be accomplished by reversing the direction of flow of process fluid by pump 314, emptying part 310. This requires that the air-pockets 324 in part 316 extend below return outlets 322.

EXAMPLE 1

A ten-loop device was utilized in this experiment. The two plates characterizing the device were identical, each including five semicircular cavities having a diameter of 0.250 inches and a length of 1 inch. The center-to-center spacing of the cavities was 0.270 inches, and thus, the bridge between the cavities was 0.020 inches. When assembled face-to-face, the cavities were offset by a length of half a cavity width with respect to each other. Each end-plate also contained an electrode compartment with a platinum wire electrode. The septum was a nylon monofilament screen having an effective pore size of 15 microns, and the electrode compartments were separated from the cavities by dialyzing membranes. A 12 channel peristaltic pump and 12-pulse-traps assembly completed the apparatus. The recycling flow rate was 1.5 ml/min/channel.

In the first experiment, a three component buffer was utilized, comprising 3 mM arginine, 10 mM d-cyclo-serine, and 4 mM p-aminobenzoic acid, pH 5.9. The electrolytes were 1.5 ml of 0.1M NaOH in the cathodic compartment and 1.5 ml of 0.1M phosphoric acid in the anodic one. The protein sample comprised 10 mg of human hemoglobin, naturally red, and 8 mg of bovine albumin, stained blue by the addition of minute quantities of bromo-phenol-blue dye. The inventors have often used such a system as a preliminary test of instrument function. While the separation is easy, the intense color permits observation of instrument performance.

The total priming volume was 14 ml, the priming having been carried out as described in FIG. 5. Focusing was started with 750 volts, resulting in a current of 15 mAmp. Within 30 minutes, at room temperature, a clear separation was observed, all the red color having been concentrated in the first channel 1 and all the blue color in the eighth channel. This was confirmed by collection of fractions achieved by a 180 degree turn of the pulse-trap assembly.

EXAMPLE 2

A more challenging separation was utilized in the second experiment, using the same apparatus. The protein sample was a commercial preparation of carbonic anhydrase. This enzyme comprises a plurality of closely spaced isoelectric fractions, differing from each other by only about 0.1 to 0.2 pH units. The same electrolyte buffers were used, but the fractionation was carried out in a solution of 30 mM MOPS, a so-called Good buffer, and 70 mM gamma-amino n-butyric acid. The run was started at 755 volts, 18 mAmp. Within 20 minutes the power was increased to 1000 volts, 14 mAmp, and at 60 minutes, the applied power was still 1000 volts, but the current decreased to 2 mAmp. The collection of the 10 fractions, carried out by reversing the orientation of the pulse traps, revealed the following pH values:

| Fraction | pH |
|---|---|
| 1 | 6.88 |
| 2 | 6.87 |
| 3 | 6.64 |
| 4 | 6.10 |

| Fraction | pH |
| --- | --- |
| 5 | 5.97 |
| 6 | 5.82 |
| 7 | 5.73 |
| 8 | 5.45 |
| 9 | 4.88 |
| 10 | 2.76 |

This pH profile corresponded to the expected values for the buffer used. A protein analysis carried out by conventional gel focusing technique revealed virtually no proteins in fractions 1 and 2, a single band in fraction 3, with increasing concentration of acidic proteins in fractions 4 to 7, and completely different acidic protein bands in fractions 8–10.

What is claimed is:

1. A multi-channel separation device, comprising:

two mating elements, at least one of which comprising an array of at least three cavities, said cavities including a first cavity and a last cavity and being arranged to define a serpentine fluid pathway through said cavities between the first cavity and the last cavity when said elements are mated, each cavity including a fluid input port and a fluid output port;

means for streamlining fluid flow from the input port to the output port of each cavity by restricting free fluid flow but not preventing solute transport between adjacent cavities; and means for establishing an electric field across said cavities.

2. The multi-channel separation device of claim 1, wherein said means for establishing an electric field comprise electrodes housed in anodic and cathodic compartments located proximate to said first and last cavities, respectively, each said compartment being separated from the respective first and last cavities by a membrane permeable to current carrying ions but impermeable to gross fluid flow.

3. The multi-channel separation device of claim 1, wherein said means for streamlining comprises a narrow passage between said elements.

4. The multi-channel separation device of claim 1, wherein both elements include cavities arranged to define the serpentine fluid pathway when said elements are mated, wherein the said cavities on one element face the cavities on the other element and each cavity on said one element is positioned to be offset from a cavity on said other element by a distance of approximately half the width of said cavities.

5. The multi-channel separation device of claim 4, wherein said means for streamlining comprise a septum positioned between said elements.

6. The multi-channel separation device of claim 5, wherein said septum comprises a monofilament screen.

7. The multi-channel separation device of claim 5, wherein said septum comprises a filter.

8. The multi-channel separation device of claim 5, wherein said septum comprises a fritted disk.

9. The multi-channel separation device of claim 5, wherein said septum comprises a membrane.

10. The multi-channel separation device of claim 5, wherein said septum comprises a gel.

11. The multi-channel separation device of claim 5, wherein said septum comprises a buffered gel.

12. The multi-channel separation device of claim 11, wherein said buffered gel comprises a covalently bound buffering agent forming a pH gradient.

13. The multi-channel separation device of claim 1, wherein said elements each comprise an elastomer allowing for disposable utilization thereof.

14. The multi-channel separation device of claim 13, further comprising two rigid end plates, wherein said elements are disposed between said end plates.

15. The multi-channel separation device of claim 14, wherein said elements are disposable and removably insertable between said end plates.

16. An apparatus for isoelectric focusing or electrophoresis, comprising:

a multi-channel separation device including two mating elements, at least one of said elements comprising an array of at least three cavities, said cavities including a first cavity and a last cavity and being arranged to define a serpentine fluid pathway through said cavities from the first cavity to the last cavity when said elements are mated, each cavity including a fluid input port and a fluid output port; means for streamlining fluid flow from the input port to the output port of each cavity by restricting free fluid flow but not preventing solute transport between adjacent cavities; means for establishing an electric field across said cavities; and means for transmitting process fluid through said cavities.

17. The apparatus of claim 16, wherein said means for transmitting process fluid comprises a set of recycling loops including a separate recycling loop for each said cavity in said device; and pumping means connected with each loop for recycling process fluid during the operation of the apparatus.

18. The apparatus of claim 17, further comprising a multiple pulse trap array including a separate sealable pulse trap connected to each loop.

19. The apparatus of claim 18, further comprising means for rotating said multiple pulse trap array about a horizontal axis, and wherein said array of pulse traps have sufficient volume capacity to prime all said recycling loops of said apparatus with process fluid when oriented in a first direction when said pumping means are activated, and said array of pulse traps collecting the fluid from all said recycling loops when said array is oriented in a direction opposite said first direction while maintaining fluid recycling in the same direction.

20. The apparatus of claim 18, wherein the pump means include means for reversing the direction of process fluid flow in each loop from one direction for priming and running the apparatus to an opposite direction for collection of separated fractions.

21. The apparatus of claim 16, further comprising cooling means incorporated in said device.

22. The apparatus of claim 16, further comprising cooling means incorporated in said recycling loops.

23. A multi-channel separation device, comprising:

two rigid end plates;

two elastomeric mating elements disposed between said end plates, each element including an array of cavities extending therethrough, said cavities being arranged to define a serpentine fluid pathway when said elements are mated, each cavity being connected to a fluid input port and a fluid output port for transfer of fluid through said cavity;

a septum disposed between said elements for streamlining fluid flow between said input and output ports of each cavity by restricting free fluid flow but not preventing solute transport between adjacent cavities; and means for establishing an electric field across said fluid pathway.

24. The multi-channel separation device of claim 23, wherein said cavities include a first cavity and a last cavity at opposite ends of said fluid pathway, and wherein said means for establishing an electric field comprise an electrode adjacent each said first and last cavity.

25. The multi-channel separation device of claim 23, wherein each cavity in one of said elements is offset from a cavity in the other of said elements by a distance of approximately half the width of the cavities.

26. The multi-channel separation device of claim 23, wherein said septum comprises a monofilament screen.

27. The multi-channel separation device of claim 23, wherein said septum comprises a filter.

28. The multi-channel separation device of claim 23, wherein said septum comprises a fritted disk.

29. The multi-channel separation device of claim 23, wherein said septum comprises a membrane.

30. The multi-channel separation device of claim 23, wherein said septum comprises a gel.

31. The multi-channel separation device of claim 23, wherein said septum comprises a buffered gel.

32. The multi-channel separation device of claim 23, wherein said buffered gel comprises a covalently bound buffering agent forming a pH gradient.

33. The multi-channel separation device of claim 23, wherein said elements are disposable and removably insertable between said end plates.

34. The multi-channel separation device of claim 23, wherein said means for establishing an electric field comprise electrodes housed in anodic and cathodic compartments, each separated from the fluid pathway by a membrane permeable to current carrying ions but impermeable to gross fluid flow.

* * * * *